United States Patent [19]

Keller

[11] Patent Number: 4,795,612

[45] Date of Patent: Jan. 3, 1989

[54] APPARATUS FOR THE DETECTION OF FILTERABLE GAS CONTAMINANTS

[75] Inventor: Manfred Keller, Jülich, Fed. Rep. of Germany

[73] Assignee: Kernforschungsanlage Julich Gesellschaft mit beschrankter Haftung, Julich, Fed. Rep. of Germany

[21] Appl. No.: 75,209

[22] Filed: Jul. 17, 1987

Related U.S. Application Data

[63] Continuation of Ser. No. 781,110, Sep. 27, 1985, abandoned.

[30] Foreign Application Priority Data

Oct. 6, 1984 [DE] Fed. Rep. of Germany ....... 3436800

[51] Int. Cl.⁴ .................. G01N 1/22; G01N 35/02; G01T 1/167
[52] U.S. Cl. .................................. 422/64; 422/88; 422/101; 73/863.23; 250/328
[58] Field of Search .......... 55/294; 73/863.21, 863.23; 250/328; 422/88, 64, 66, 101; 436/44, 45

[56] References Cited

U.S. PATENT DOCUMENTS

| | | | |
|---|---|---|---|
| 1,944,267 | 1/1934 | Rathbun | 55/294 |
| 3,863,072 | 1/1975 | Garin et al. | 250/370 |
| 3,926,593 | 12/1975 | Squires et al. | 55/96 |
| 4,056,818 | 11/1977 | Oddsen | 340/309.4 |
| 4,088,737 | 5/1978 | Thomas et al. | 423/240 |
| 4,236,070 | 11/1980 | Lee | 250/231 SE |
| 4,250,531 | 2/1981 | Ahrens | 361/2 |
| 4,260,892 | 4/1981 | Kovacs et al. | 250/388 |
| 4,266,953 | 5/1981 | Matthys et al. | 55/294 |
| 4,290,786 | 9/1981 | Schuff | 55/107 |
| 4,401,889 | 8/1983 | Buus et al. | 422/64 X |
| 4,462,399 | 7/1984 | Braun | 128/201.25 |
| 4,510,929 | 4/1985 | Dordoni et al. | 128/200.14 |

FOREIGN PATENT DOCUMENTS

| | | | |
|---|---|---|---|
| 1108818 | 6/1961 | Fed. Rep. of Germany. | |
| 1147326 | 4/1963 | Fed. Rep. of Germany. | |
| 1321571 | 2/1963 | France | 250/328 |
| 1484728 | 6/1976 | France | 250/328 |
| 57-110974 | 7/1982 | Japan | 250/328 |
| 1191982 | 5/1970 | United Kingdom | 250/328 |

Primary Examiner—Michael S. Marcus
Assistant Examiner—Richard D. Jordan
Attorney, Agent, or Firm—Nils H. Ljungman

[57] ABSTRACT

For the determination of filterable pollutants in gases there is a filter disc, which is located on a horizontal, compact rotary plate, which is moved over a suction head, whose suction lips interact with corresponding holes or borings in the rotary plate. The suction head is pushed upon from underneath by action of a universal-joint spring bearing against the plane-parallel rotary plate. Preferably, the rotary plate is rotated each time in steps at determined cycle times, specifically according to a program, by a determined number of collection spaces with "phase-shifted" multiple rotations of the plate, until the filter surface is completely used up. Instead of a filter disc, absorber material can also be used for radioactivity monitoring with a forward motion cycle of 1 to 2 days. Three detectors are provided, with the first detector being typically disposed above a first space, the second detector disposed above a space three spaces from the first space, and the third detector disposed above a space eleven spaces from the first space, for example, if the rotary plate is always moved forward by 2 spaces after the accumulation of the specimen in the first space.

23 Claims, 8 Drawing Sheets

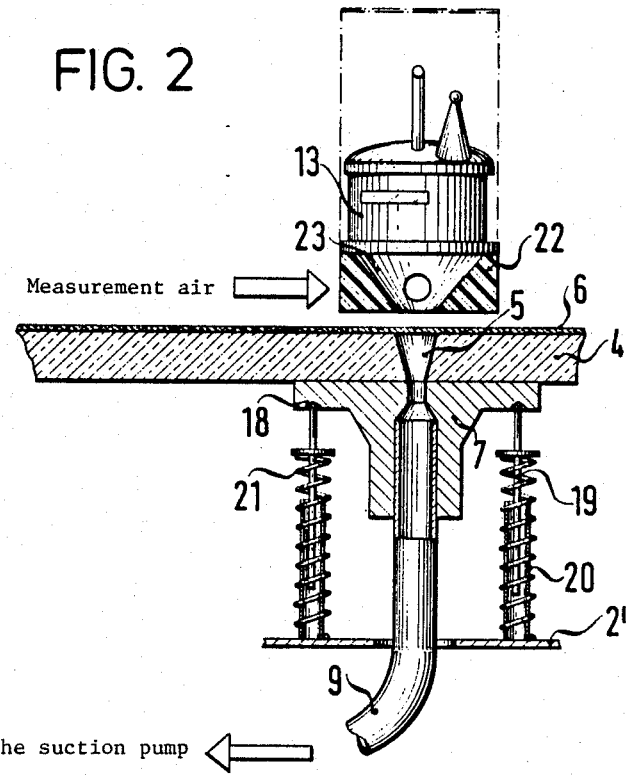
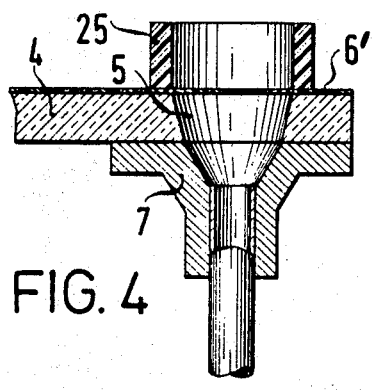
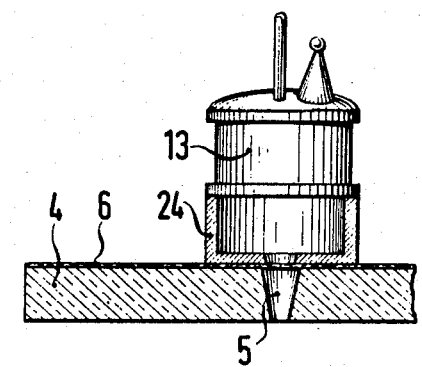

APPARATUS FOR THE DETECTION OF FILTERABLE GAS CONTAMINANTS

This application is a continuation of U.S. application Ser. No. 781,110, filed on Sept. 27, 1985, and now abandoned.

BACKGROUND OF THE INVENTION

1. Field of the Invention

The invention relates to an apparatus for the detection of filterable gas contaminants and, more particularly, to such apparatus with a circular filter track which can be moved by action of a horizontal compact rotary plate over a suction pump with pump connection.

2. Description of the Prior Art

Such an apparatus is known from German Patent Publication Published for Opposition Purposes No. DE-AS No. 1 108 818, but this apparatus experiences problems involving forward movement, especially with relatively thin filter discs. This Federal Republic of Germany patent application published for opposition purposes and any patent issuing therefrom are incorporated herein by reference.

The detection of impurities, especially of pollutants in air, has been important for a long time, and has recently attracted increasing attention. Many contaminants can be filtered out of the air. Some, like aerosols or dusts, can be "screened" by an appropriate filter or collected by sorptive deposition on sorbents, such as activated carbon or zeolite. The detection of the concentrated pollutant on the filter or sorbent can be performed chemically or specifically by a physical-chemical analysis technique such as fluorescence analysis or a similar process.

In the area of monitoring of radioactivity, such a detection of air pollutants plays an altogether special role. Its sensitive detection of the radiation emitted is possible with the use of appropriate radiation-sensitive detectors.

Thus, there are presently devices for the detection of radioactive dusts and aerosols, in which a strip-like filter running over rollers is pulled in a stepwise manner over a gas-permeable support, which is connected with a suction system after the conclusion of the forward movement. Such an apparatus, with a constant forward movement, is described in German Patent Publication Published for Opposition Purposes No. DE-AS No. 1 147 326. The design of this known apparatus is relatively complicated, and its operation is not entirely satisfactory. This Federal Republic of Germany patent application published for opposition purposes and any patent issuing therefrom are incorporated herein by reference.

OBJECTS OF THE INVENTION

An object of the invention is to provide an apparatus for the detection of gas contaminants.

A further object of the invention is to provide an apparatus for filtering out gas contaminants.

A yet further object of the invention is to provide an apparatus which operates as simply and reliably as possible.

A still further object of the invention is to provide an apparatus which offers possibilities of modification and which is specifically suited for operation over long, uninterrupted periods of time.

A yet still further object of the invention is to provide an apparatus which can be made maintenance-free.

SUMMARY OF THE INVENTION

These objects are achieved by the apparatus described by the invention in that a compact rotary table, which supports the entire filter, collects the contamination. There are holes or borings, along the circular track, which interact with the lip shape of the suction head. The suction head is pressed against the plane-parallel rotary table from below by means of a universal spring bearing.

On such a horizontal rotary filter, with a suction head being elastically supported from below by a "compensation bearing", the operation of the apparatus is significantly simplified, since both continuous and step-wise forward movement of the filter becomes possible. In the latter case, no separation from the pump system is necessary. In the embodiments of the invention, it is particularly important that the forward movement of the filtrant always takes place jointly with the support. Thus, the filtrant is not subjected to any tensile forces.

In other words, the rotary table can be rotated continuously by a motor drive, or can be moved forward by means of a step motor. Such a step-wise forward movement can be achieved, for example, by means of a solenoid. The solenoid activates a pusher mechanism, which engages a gear wheel rigidly connected with the rotary table, and which moves the rotary table forward by a determined angle. An example of a solenoid stepper drive is found in U.S. Pat. No. 4,056,818, which patent is incorporated herein by reference. Alternately, the step-wise forward movement can also be controlled by means of apertured plates and photoelectric sensors. An example of a phototransistor system is found in U.S. Pat. No. 4,236,070, which patent is incorporated herein by reference.

The holes or borings provided on the rotary plate, which interact with the suction head, preferably have a ring of adjacent, generally oval radial slits, which are tapered toward the bottom. The suction head also has a radial slit located inside a relatively wide "suction lip", which corresponds to the cross section of the bottom of the radial slits of the holes or borings on the rotary plate, although the slit of the suction head is preferably slightly larger. To keep the friction between the rotary plate and the suction head low, materials such as Plexiglas ® (polymethacrylate) or Teflon ® (polytetrafluoroethylene) can be used. To achieve a tight fit of the suction head against the rotary plate, the contact surfaces must preferably be worked flat and smooth.

The collecting capacity of such a filter is relatively large and makes possible continuous operation over long periods of time, especially if two rotary filters, which can be operated alternately, are present in a single apparatus.

For an exact determination of the contaminants, which are generally comprised of several components; various detectors are necessary. Radioactive mixtures may also require additional delayed measurements. Therefore, such a collection and measurement apparatus is preferably equipped with several detectors, which, because of their space requirements, are usually offset at angles from one another around the rotary filter. If the collection apparatus, for example, includes a first detector, by means of which the contaminant content can be measured even as the specimen is being taken, and a second detector by means of which the contaminant content can be measured immediately after the specimen is taken, then with a forward movement of the rotary filter by a narrow collection space, then the specimen cannot be moved sufficiently to reach this second detector immediately after the sampling. Preferably, therefore, a programmed forward movement is executed by a corresponding number of collection spots, which then brings a collected specimen directly below this detector.

Moreover, to achieve maximum utilization of a measurement filter located on the rotary table, a number n of slits are made in the rotary table, which is equal to $z \cdot \Delta n + 1$ or $z \cdot \Delta n - 1$, whereby $\Delta n$ is the distance between the collection space and the detector (measured in number of slits), and z the number of specimens taken per rotation of the table. An additional requirement is that $n+1$ or $n-1$ not be a prime number.

With such an embodiment, a fixed forward movement program makes maximum use of the rotary filter, since the location of the sampling moves forward or backward by one specimen space per rotation of the table.

Appropriate detectors for the determination of filterable radioactive air pollutants are the customary radiation measurement probes, such as Geiger-Mueller counters, proportional counters, scintillation detectors or semiconductor detectors. Several of these detectors can be used on the same apparatus, arranged at angles over the filter, at an interval which corresponds to the forward movement of the rotary plate between the two samplings, or by a whole number multiple thereof. By means of such additional detectors, it is possible to obtain data concerning the half life of the radioactive materials collected and/or the energy of the radiation emitted.

Non-radioactive specimens can be analyzed for their fluorescence behavior or similar characteristics.

The air filter or measurement filter provided on the rotary plate can preferably be a glass fiber paper or membrane filter, suitable for the collection of aerosol particles. Alternatively, filter discs with a selective collection capability can be provided. For the measurement of impurities which can be concentrated by sorption, for example, on granulates such as active carbon or silver zeolite, the rotary plate itself may have containment means or an insert with cup-like holes or filter chambers. The cup-like holes can be designed as countersunk holes. The bottoms of these holes are perforated and appropriately covered with a filter paper.

To prevent the suction of secondary air through the air filter, the rotary plates are preferably installed in an airtight housing, which has an inlet opening and a tube or hose connected with the inlet, and a guide hood over the suction head. Such a housing has a separate chamber for each rotary filter, in which the rotary filter is mounted on rails so that it can be extracted.

With such a twin configuration of two rotary filters, there can be a common pump system, if appropriate, to which the two suction heads are connected by means of a two-way valve.

BRIEF DESCRIPTION OF THE DRAWINGS

The invention is explained below on the basis of embodiments, with reference to the attached drawings, which show schematically:

FIG. 2 is a cross sectional view of a mounting of a suction head below a rotary plate and a detector located directly above a collection point;

FIG. 3 is a cross sectional view of a detector for use in an embodiment of the invention;

FIGS. 4 to 7 are cross sectional views of alternative embodiments of the invention for collection of air pollutants;

DESCRIPTION OF THE PREFERRED EMBODIMENTS

Figure 1:
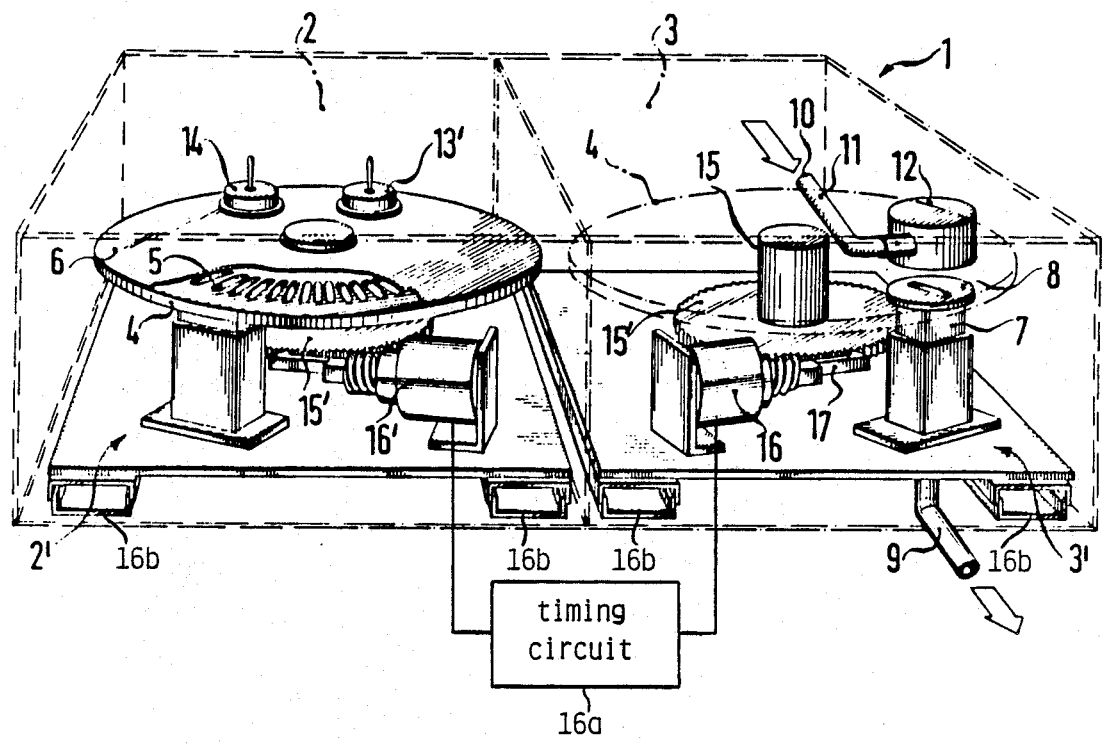
FIG. 1 is a perspective view of an embodiment of the invention having two rotary filters, each in its chamber, in a two-chamber housing.

As can be seen in FIG. 1, the housing 1 comprises two chambers 2 and 3. In each of these chambers 2 and 3, there is a rigid, flat rotary table 4, approximately 10 mm thick, made of Plexiglas ® or Teflon ®, which is 20 cm in diameter. The rotary table 4 has radial slits 5, on top of which there is disposed an aerosol filter 6. In the present embodiment, the radial slits 5 are rounded at their ends and disposed with their longitudinal axes along radii of the rotary table 4. Under the rotary table 4, there is a suction head 7, preferably made from polytetrafluorethylene, with suction lips 8, which suction head 7 is connected via a line 9 to a suction system (not shown). The gas or air to be filtered is sucked in through a housing opening 10, which is connected via a line 11. A "hood" 12, which is connected to the line 11, is disposed above the sampling point. Two detectors 13' and 14 are preferably disposed above the aerosol filter 6 at locations displaced from the hood 12, which are not illustrated here in any further detail. Examples of detectors are found in U.S. Pat. Nos. 4,510,929; 4,462,399; 4,290,786; 4,260,892; 4,250,531; 3,926,593; and 3,863,072. All of the aforementioned U.S. Patents are incorporated herein by reference.

The rotary plate 4 is rigidly connected by means of a shaft 15 to a circular plate with a toothed rim 15', which is activated and rotated by signal-controlled solenoid lifting magnets 16 and 16'. The solenoid lifting magnets 16 and 16' are used as pushing mechanisms for a tooth or driver 17, which engages the toothed rim 15' of the circular plate of each of the chambers 2 and 3. The signal-controlled solenoid lifting magnets 16 and 16' are connected to a timing circuit 16a, which has circuitry to energize one lifting magnet 16 during a first sequence, and the other lifting magnet 16' during a second sequence of operation.

The rotary table configuration is mounted on a base plate 2' or 3', respectively. The base plates 2' and 3' are carried on rails 16b, and can therefore be extracted from the front when the chambers 2 and/or 3 are equipped with a removable front plate (not shown).

FIG. 2 shows a sectional view looking towards the center of the rotary plate 4 with the "compensation bearing" of the suction head 7, which has two indentations 18 on its underside. Upwardly extending pins 19 have their upper tips extending into the indentations 18. The pins 19 can slide inside guide sleeves 20, and are pressed into the indentations 18 by helical springs 21, the lower ends of which are preferably wound around the guide sleeves 20 and are in contact with the base plate 2'. The helical springs 21 have ends which are in contact with and press the pins 19 upwardly.

FIG. 2 also shows the conical form of the radial slits 5 which taper with decreasing diameter toward the bottom, as well as a detector 13 located immediately above the collection point, which can be formed by an end-window counter tube or similar apparatus.

Between the rotary aerosol filter 6 and the detector 13, there is disposed a shield or screening like air duct 22 with a hole 23 therein. The air duct 22 can be connected by means of the line 77, such as a hose, such that air or gas can be sucked into the filter 6. By this means, pollutants in the air (or the gas) caught by the aerosol filter 6 can be monitored by the detector 13 thereabove.

FIG. 3 shows the configuration of the detector 13 above a specimen previously collected on the aerosol filter 6. In this configuration, there is a shield 24 between the aerosol filter 6 and the detector 13, by means of which it is possible to reduce the effect of neighboring specimens on the determination of the activity of the specimen immediately below.

FIGS. 1 to 3 show the configuration described by the invention with a dust or aerosol filter. Alternatively, however, the sorption material can be located above the suction head 7.

As shown in FIG. 4, when the sorption material is located above the suction head 7, ring inserts 25 are preferably placed above the recesses or radial slits 5 in the rotary plate 4 (shown as a circular hole in FIG. 4). A filter paper or a filter mat 6' is placed between the ring inserts 25 and the rotary plate 4. These ring inserts 25 then form cups, with the filter mat 6' forming the bottom of the cups, into which adsorption material can be placed.

Figure 5:
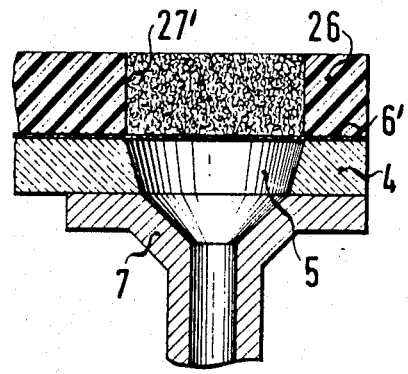

The configuration illustrated in FIG. 5 is more efficient than the very simple type of embodiment in FIG. 4. In the embodiment of FIG. 5, above the rotary plate 4 with the filter mat 6', there is disposed an attachment or headpiece with borings 26, which are preferably filled with granular sorption material 27'. The borings 26 are located opposite the slits or holes 5 of the rotary plate 4. The suction head 7 is disposed below the rotary plate 4.

Figure 6:
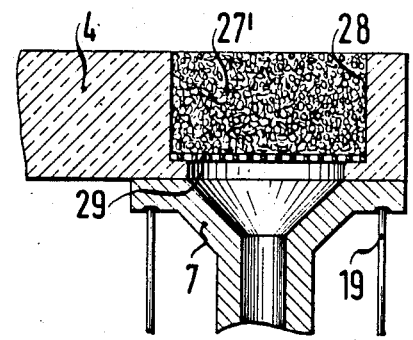

Alternatively, as shown in FIG. 6, the rotary plate 4 itself can be provided with countersunk holes 28, each being closed by a perforated plate 29, and which thus form cup-like recesses into which the sorption material 27' can be placed. Instead of the countersunk holes 28, it is also possible to provide a recess with a filter disc inserted therein.

Figure 7:
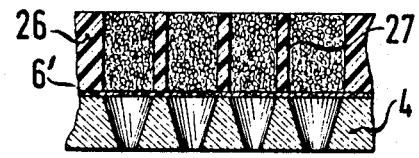

A configuration similar to that shown in FIG. 5 is shown in FIG. 7, in which the borings 26 of the headpiece filled with sorption material 27', formed when the filter mat 6' is also used, are adapted to the configuration of the radial slits 5 (as shown in FIG. 1).

Figure 8:
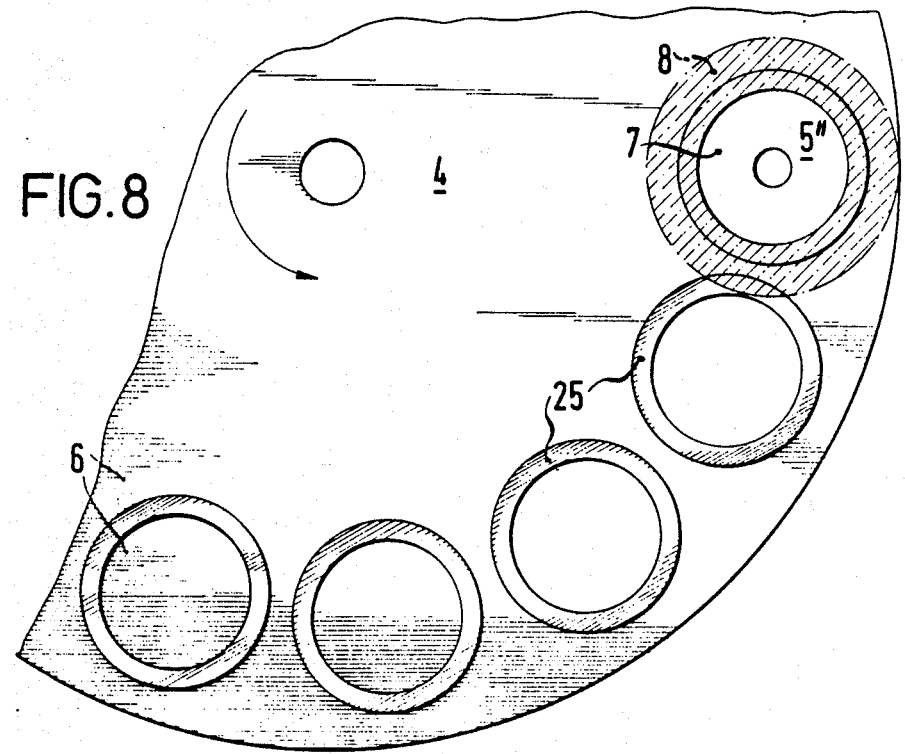
FIGS. 8 to 12 are plan views of suction head embodiments and different rotary plate holes according to the invention.

FIG. 8 shows a schematic view of a rotary plate 4 with the ring inserts 25 placed over the nearly cylindrical holes 5" (covered by a filter mat 6'). The suction head 7 is indicated by shaded lines having suction lips 8.

Figure 9:
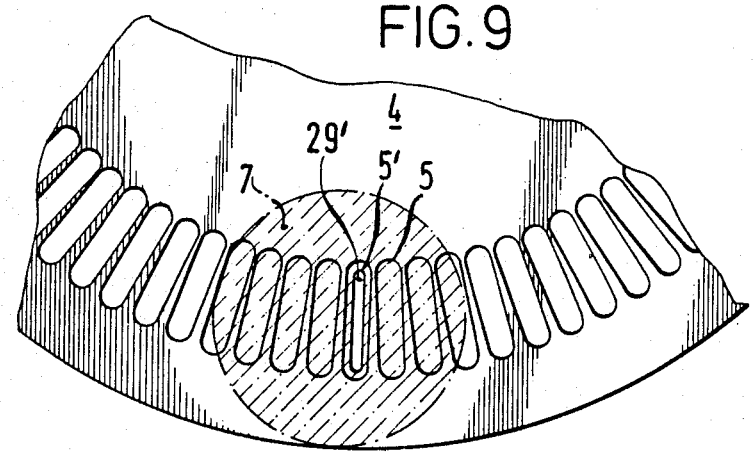

FIG. 9 shows a rotary plate 4 with an annular region of radial slits 5 disposed above the suction head 7 (shown by shaded lines). The suction head 7 has a relatively wide lip. The suction head 7 has a suction opening 29' which is adapted to align with an opening of a tapered lower cross section 5' of an aligned radial slit 5 on the underside of the rotary plate 4, such as the radial slits 5 in FIG. 2. Most of the tapering is not shown in the drawing. FIG. 9 shows a suction lip of considerable width. Generally, however, it is desirable not to make the suction lips too wide, to avoid sealing problems.

Figure 10:
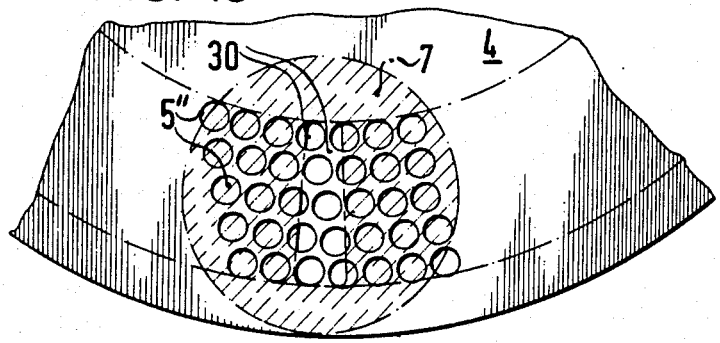
Figure 12:
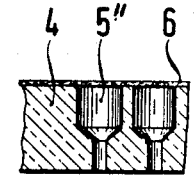

As shown in FIG. 10, the rotary plate 4 has, near the circumference thereof, a relatively wide ring of small cylindrical borings or holes 5". FIG. 12 shows these holes 5" (shown shaded), which can be, but need not be, tapered or countersunk toward the bottom thereof. The suction head 7 with a suction slit 30, disposed directly above the rotary plate 4, interacts with such a perforated annular region of the rotary plate 4. This concept is essentially intended for use with a slow continuous movement of the rotary plate 4.

Figure 11:
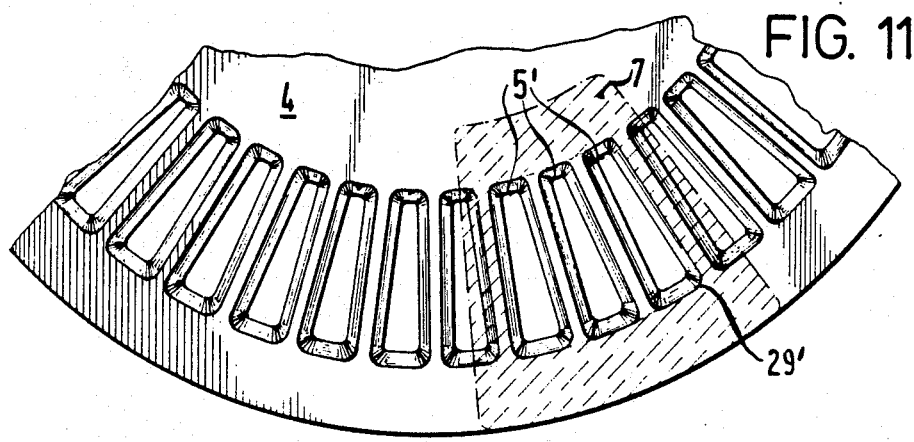

For use with a continuous movement of the rotary plate 4, the configuration shown in FIG. 11 would also be suitable, in which the suction opening 29' of the suction head 7 (shown shaded) covers three or more radial slits 5, and in which the suction lip is wider than the tapered lower cross section 5' of the radial slit borings of the rotary plate 4. This configuration, too, is suitable for quasi-continuous air filtration.

An embodiment such as that illustrated in FIG. 9, which preferably has glass fiber paper aerosol filter installed, was used for the detection of radioactive aerosol and dust particles. The duration of collection for each sampling point was set at 24 hours in this embodiment. This embodiment was equipped with end-window counter tubes offset from one another at appropriate angles, specifically: with a first counter tube on space one, which determines the aerosol activity even as the specimen is being taken; with a second counter tube reached (immediately after the sampling) located preferably above the space eight which, after the sampling is completed and the rotary table has moved forward by preferably seven sampling spaces (for a repeated sampling), begins the measurement; and with a third counter tube on space forty three, by means of which the activity is measured after another five days.

As a result of the step motion of the rotary plate for the next sampling, by the action of the lifting magnet 16 (as shown in FIG. 1), an area of the filter which is seven filter spaces farther on is moved to a portion over the suction head 7.

The radio-iodine level in the environmental atmosphere was monitored with silver-zeolite sorbents, as shown in FIG. 6.

Silver-zeolite sorbents are discussed in U.S. Pat. No. 4,088,737, which is incorporated herein by reference.

For an early determination of very small concentrations of aerosol beta activities of "non-natural" origin (artificial, industrial, caused by human activity), a configuration with 3 detectors is particularly well-suited, in which the first detector 13 is located immediately above the suction point, and is used for current or immediate monitoring. This detector 13 is specifically designed to provide immediate information when important or emergency events occur.

The second detector, such as the detector 13', is reached by the step-wise forward movement after the end of the collection period, and provides data on the subsequent decay behavior, while the third detector, such as the detector 14, determines the long-lived total beta activity concentration at the measurement point.

The air throughput is appropriately 1 $m^3/h$ and a sampling time between two step motions of the rotary plate 4, of 1 to 2 days, can be selected for the accumulation of the radioactive contamination.

On a rotary plate 4 which, in one embodiment, always backs up by two spaces, the above-mentioned detectors 13, 13' and 14 can be installed, for example, with the first detector 13 being typically disposed above a first space, the second detector 13' (on place 3) disposed above a space two steps of the lifting magnet 16 displaced from the first space, and the third detector 14 disposed above a space eleven, ten steps of the lifting magnet 16 displaced from the first space. Though superimposed on the non-naturally occurring activity, the naturally occurring activity RaB and ThB are to be taken into special consideration in measurements of beta activity. The ratio of these substances (belonging to different decay series) is subject to atmospheric conditions. Using the known half-lives of these two natural isotopes, the superimposition of artifically occurring radioactivity can be determined with relatively high precision from already determined decay curves, with reference to the corresponding ThB curves, or by means of a computer with this information programmed therein.

The basic idea of this process relates to eliminating the short-lived RaB from the natural RaB/ThB mixture as a function of the radioactive decay status. After approximately 2 to 3 hours, practically all that remains in the dust specimen is the naturally occurring ThB portion with a known half-life of 10.6 hours, and the unknown long-lived activity of non-naturally occurring origin to be detected.

To optimize the design parameters, the length of time for the decay analysis should preferably be 2 to 4 half-lives of the ThB (T ½ = 10.6 hours) — that is, 1 to 2 days. That means that during the collection time for ThB, which is equal to the interval between steps, a quasi-equilibrium is achieved, and the RaB portion (T ½ = 26.8 minutes) is already relatively low. During the decay analysis, an appropriately programmed computer compares the continuously-measured pulse rates n of the decay process with the known decay curve of ThB, which is:

$$\ln \cdot n \ (ThB) = k - 0.693 \ t/10.6$$

In this manner, long-lived aerosols can be detected, and the required detection sensitivity and accuracy achieved.

The experimental results obtained are shown in FIGS. 13 to 17. The evaluation of the specimen with 0.1 Bq (Becquerel), with an air throughput of 1 cubic meter per hour, a total metering yield of 0.2 and a collection and measurement time of 48 hours, gives a detectable activity concentration of approximately 0.001 Bq/m³, a value which meets the required limits of detection, a result which even a specialist in the field would not have expected. It should be noted that the optimum design of the rotary filter measurement system, constructed for tests, may not yet have been achieved.

With increased activity concentrations caused by an incident, the collection and decay time can be correspondingly shortened. If, for example, the concentration increases to 100 times the value of the limit of detection (double the annual dose for Sr-90), then this increase can be detected as early as after one hour.

Figure 13:
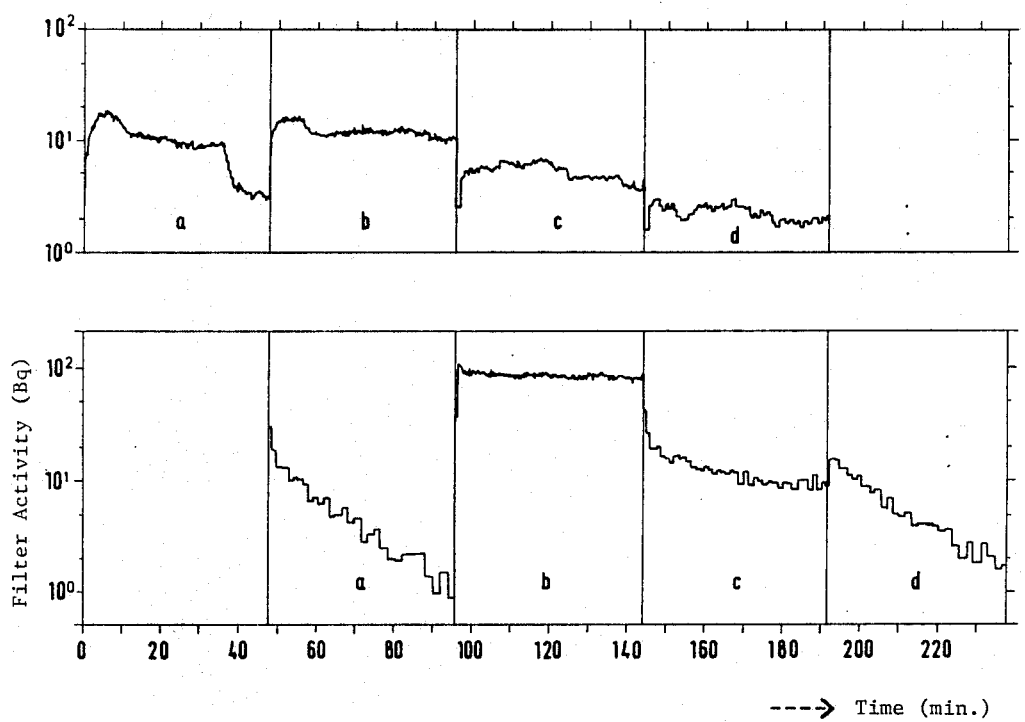
FIGS. 13 to 18 are graphic representations of activity measurement curves.

The curves in FIG. 13 illustrate the dependence of the measured collection and decay curve of airborne dust specimens on additionally superimposed long-lived radionuclides of man made origin in proportions of 10 Bq, 1 Bq and 0.1 Bq, namely:

top: Collection curves (measured with Detector I)
  bottom: Decay curves (measured with Detector II)
  (a) Airborne dust (naturally occurring aerosol, RaB and ThB)
  (b) Airborne dust, also charged with approximately 10 Bq (Sr+Y)
  (c) Airborne dust, also charged with approximately 1 Bq (Sr+Y)
  (d) Airborne dust, also charged with approximately 0.1 Bq (Sr+Y)

Figure 14:
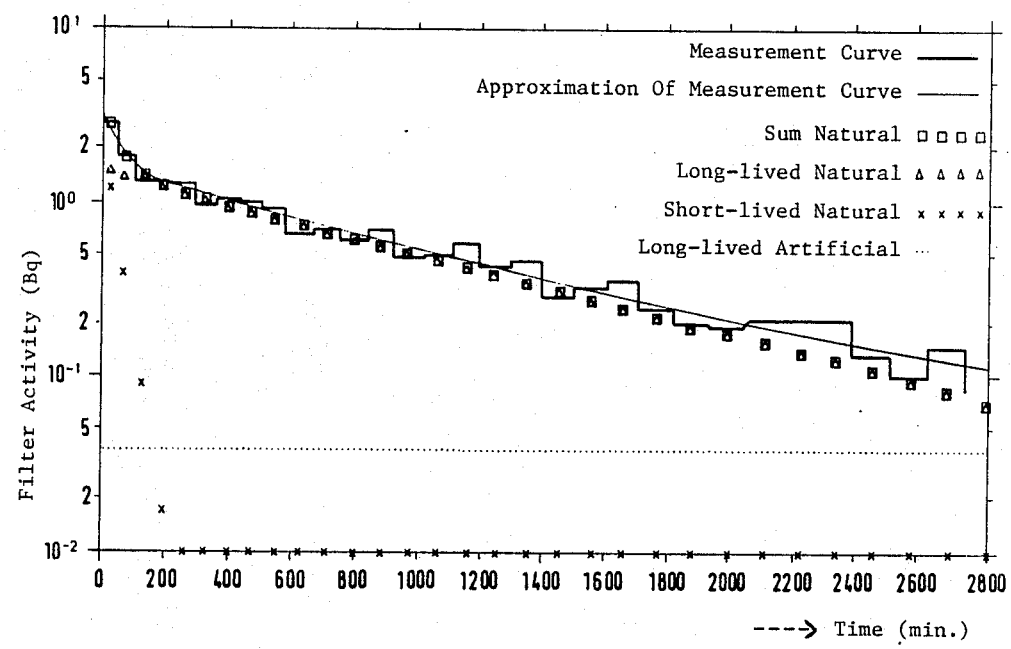
Figure 15:
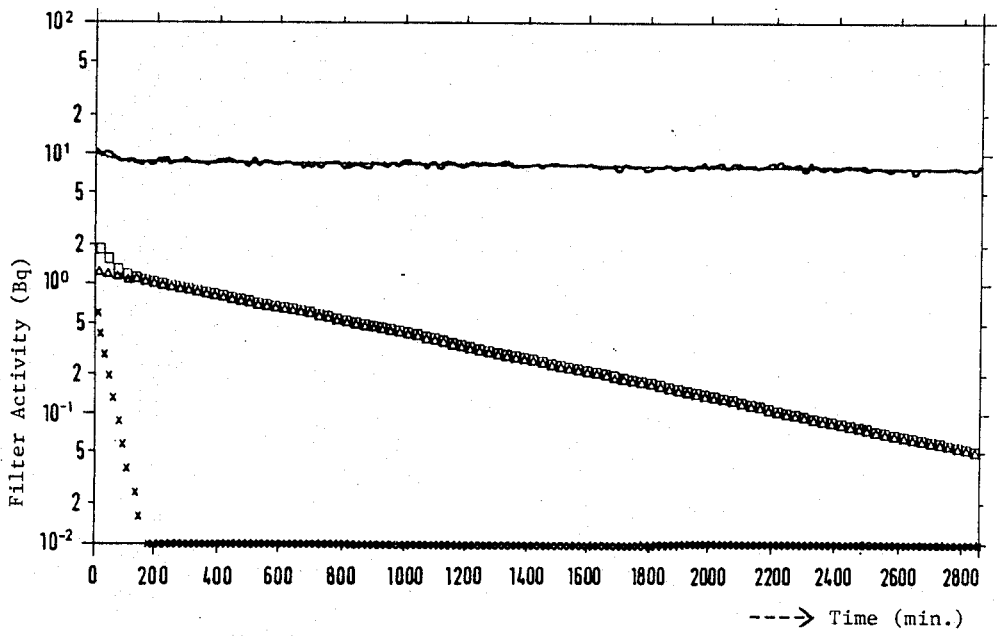
Figure 16:
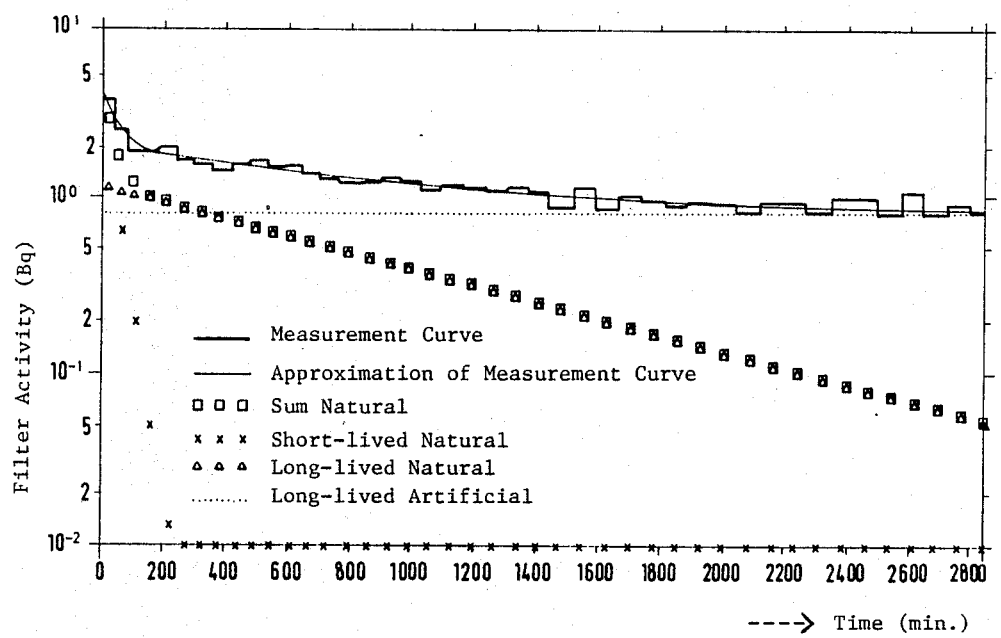
Figure 17:
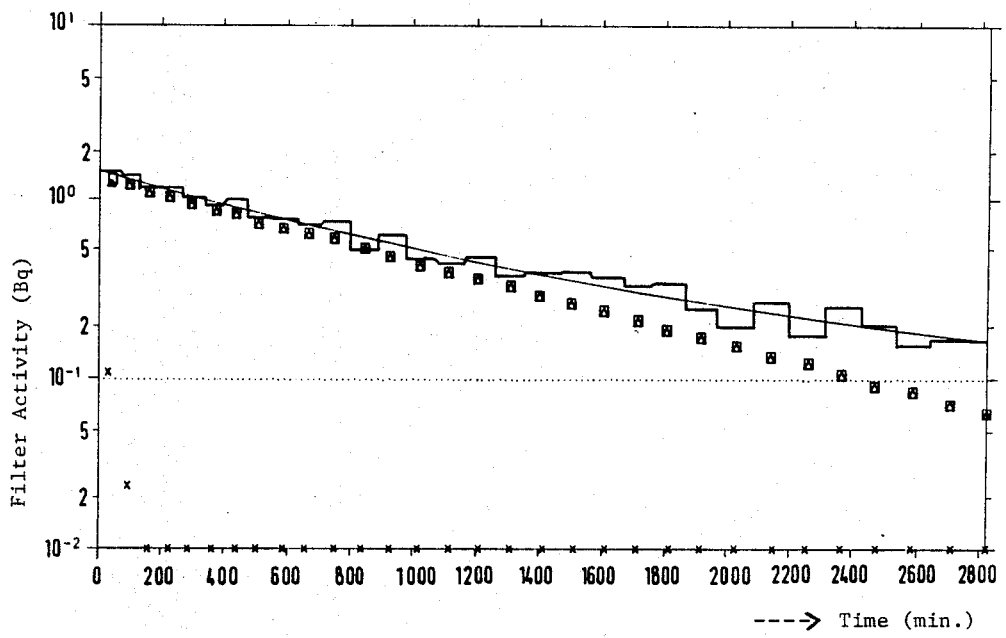

FIGS. 14 to 17 illustrate the decay analyses of the counting rates on the basis of the current dust specimen activity. FIG. 14 shows filter activity as a function of elapsed time in Becquerels (Bq) for: short-lived, naturally occurring; long-lived, naturally occurring; and long-lived, artificially occurring radiation, sampled according to the invention, and curves drawn in accordance with the measurements. Computer analyses gave the following results:

For 2.05 Bq RaB (Pb 214), with 1.5 Bq ThB (Pb 212), a 0.002 Bq long-lived residue;
  For 0.71 Bq RaB (Pb 214), with 1.21 Bq ThB (Pb 212), a 7.86 Bq long-lived portion (Sr, Y);
  For 2.6 Bq RaB (Pb 214), with 1.18 Bq ThB (Pb 212), a 0.82 Bq long-lived portion (Sr, Y);
  For 0.21 Bq RaB (Pb 214), with 1.38 Bq ThB (Pb 212), a 0.09 Bq long-lived portion (Sr, Y).

Figure 18:
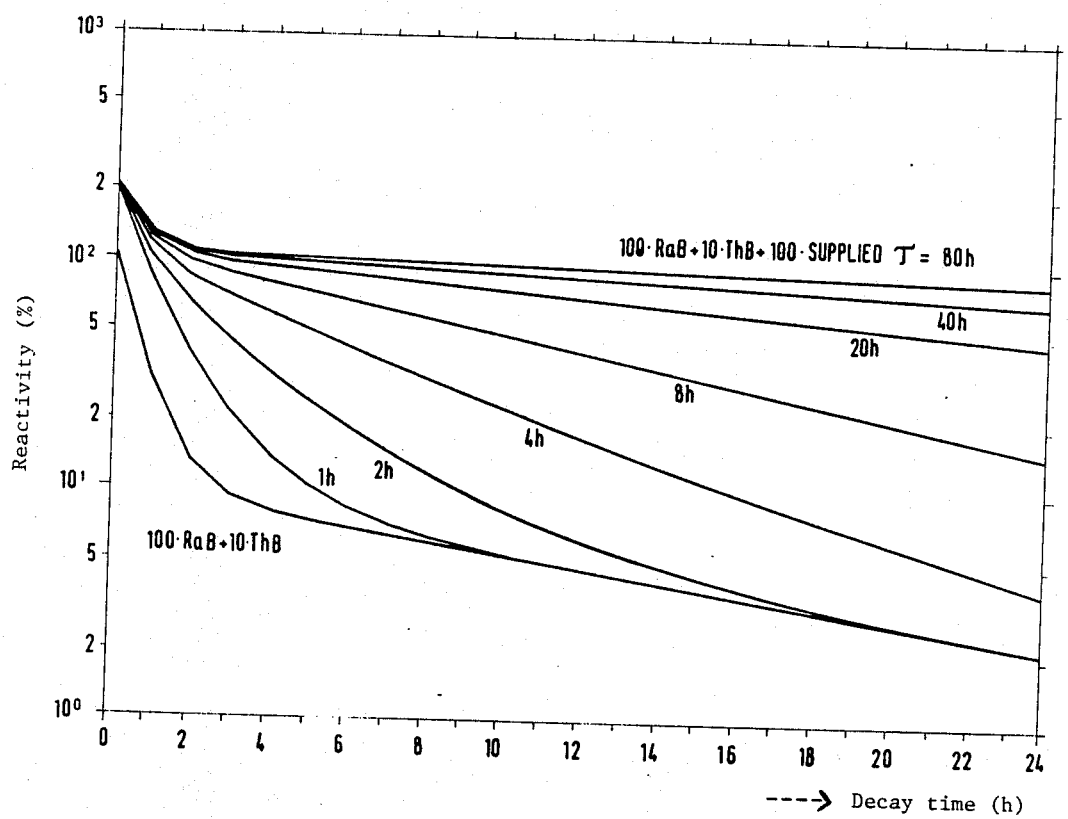

By means of the computer-assisted decay analysis, short-lived radionuclides, of non-naturally occurring origin, bonded to aerosols, can also be detected, if the half lives of these short-lived radionuclides differ from that of ThB and if there is sufficient activity present. FIG. 18, for example, shows the curves for the dependence of the decay curve of the radioactivity of radioactive specimens, comprising the natural radionuclides in the proportion of 100 parts for RaB and 10 parts for ThB, also superimposed by short-lived (artificial) radionuclides at 100 parts with half lives of 1 hour, 2 hours, 4 hours, 8 hours, 20 hours, 40 hours and 80 hours.

The invention as described hereinabove in the context of the preferred embodiments is not to be taken as limited to all of the provided details thereof, since modifications and variations thereof may be made without departing from the spirit and scope of the invention.

What is claimed is:

1. Apparatus for collection of a specimen for measurement of at least one filterable component and for determination of at least one parameter of said at least one filterable component, said apparatus comprising:

a substantially rigid rotatable plate having formed thereon a circular track of throughgoing apertures;
  a base for rotatably supporting said rotatable plate;
  a suction head disposed on a first side of said rotatable plate to draw a gas through a predetermined number of said apertures, the opposed contact surfaces of said suction head and said circular track being substantially flat and smooth to thereby minimize frictional forces between said contact surfaces;
  means for filtering disposed in contact with said circular track of apertures on a second side of said rotatable plate opposite to said first side to filter said gas drawn through said predetermined number of apertures by said suction head, said filtering means comprimising a removable continuous mat of filter material independently supported by said rotatable plate and overlaying at least said circular track of apertures;
  means for rotating said rotatable plate with respect to said base;
  means for determining at least one parameter of said at least one filterable component; and means for biasing said suction head against said rotatable plate, said biasing means having spring means for continuously aligning said suction head against said rotatable plate, said plate defining a first substantially flat planar surface and said head defining a second substantially flat planar surface disposed against said first surface;

said suction head having a lip, said lip having a width for substantially preventing binding between said head and said rotatable plate and also for providing sealing contact between said first surface on said plate and said second surface on said head, whereby leakage of gas between said suction head and said rotatable plate is minimized said head having a longitudinal axis being substantially aligned with an axis substantially perpendicular to said first surface;

said head being angularly displaceable with respect to said axis perpendicular to said first surface; and said spring means including alignment means for aligning said second surface with respect to said first surface and for providing substantially sealing contact therebetween.

2. The apparatus for collection of at least one filterable component and for determination of at least one parameter of said at least one filterable component according to claim 1 wherein said circular track of apertures comprises an annular region on said rotatable plate;

said apertures being slits;

said rotatable plate having a first flat surface and a second flat surface, and a center point of rotation about which said circular track of apertures rotate;

said slits having a length dimension greater than a width dimension thereof;

said length dimension being disposed along said first flat surface of said rotatable plate, and substantially aligned with radii extending from said center point of rotation of said circular track of apertures.

3. The apparatus for collection of at least one filterable component and for determination of at least one parameter of said at least one filterable component according to claim 2 wherein said lip surrounds an opening in said suction head, being substantially at least as large as one of said slits, and said opening in said suction head being substantially aligned to communicate with at least one of said slits.

4. The apparatus for collection of at least one filterable component and for determination of at least one parameter of said at least one filterable component according to claim 3 wherein said means for rotating said rotatable plate comprises means for stepwisely rotating said rotatable plate.

5. The apparatus for collection of at least one filterable component and for determination of at least one parameter of said at least one filterable component according to claim 2 wherein said slits are tapered, with a larger end of each said taper being disposed adjacent said first flat surface of said rotatable plate, and wherein said suction head is disposed on said second flat surface of said rotatable plate.

6. The apparatus for collection of at least one filterable component and for determination of at least one parameter of said at least one filterable component according to claim 5 wherein said means for rotating said rotatable plate comprises means for stepwisely rotating said rotatable plate.

7. The apparatus for collection of at least one filterable component and for determination of at least one parameter of said at least one filterable component according to claim 2 wherein said means for rotating said rotatable plate comprises means for stepwisely rotating said rotatable plate.

8. The apparatus for collection of at least one filterable component and for determination of at least one parameter of said at least one filterable component according to claim 1 wherein said means for rotating said rotatable plate comprises means for stepwisely rotating said rotatable plate.

9. The apparatus for collection of at least one filterable component and for determination of at least one parameter of said at least one filterable component according to claim 8 wherein said stepwise rotating means comprises another rotatable plate rigidly connected to said rotatable plate, said another rotatable plate having a toothed rim; and solenoid means for engagement with said toothed rim of said another rotatable plate, for stepwisely rotating both said rotatable plates.

10. The apparatus for collection of at least one filterable component and for determination of at least one parameter of said at least one filterable component according to claim 9 including a second apparatus, identical to said apparatus already described, and means for operating said two apparatuses alternately.

11. The apparatus for collection of at least one filterable component and for determination of at least one parameter of said at least one filterable component according to claim 8 wherein said apertures comprise n collection regions having z specimens per rotatable plate rotation the spacing of successive specimens of one rotation being $\Delta n$, with $\Delta n$ substantially full rotations of said rotatable plate to fill all said n collection regions;

said n collection regions being equal to $z \cdot \Delta n \pm 1$, where $n \pm 1$ is a non-prime number; and wherein said rotary means has means for driving said rotary plate $\Delta n$ full revolutions before a given one of said collection regions is again disposed for collection of a specimen, and wherein said collection regions, in each rotation from a first rotation, in a series to, said $\Delta n$ rotation in said series, are displaced from one another.

12. The apparatus for collection of at least one filterable component and for determination of at least one parameter of said at least one filterable component according to claim 1 including a second apparatus, identical to said apparatus already described, and means for operating said two apparatuses alternately.

13. The apparatus for collection of at least one filterable component and for determination of at least one parameter of said at least one filterable component according to claim 12 including an airtight housing for each said apparatus having its own filtering means, with separate chambers for each said apparatus thereof.

14. The apparatus for collection of at least one filterable component and for determination of at least one parameter of said at least one filterable component according to claim 1 wherein said means for determining comprises at least one contamination detector, said at least one contamination detector being angularly disposed from said suction head, such that said at least one contamination detector is disposed away from said suction head.

15. The apparatus for collection of at least one filterable component and for determination of at least one parameter of said at least one filterable component according to claim 1 wherein said apertures comprise cup-like recesses for holding a contamination concentrating material.

16. The apparatus for collection of at least one filterable component and for determination of at least one parameter of said at least one filterable component according to claim 15 wherein said contamination concentrating material comprises an adsorber material.

17. The apparatus for collection of at least one filterable component and for determination of at least one parameter of said at least one filterable component according to claim 1 including timing means connected to said rotating means for energizing said rotating means along a direction of rotation at predetermined times.

18. The apparatus for collection of at least one filterable component and for determination of at least one parameter of said at least one filterable component according to claim 17 wherein said determining means comprises three detectors angularly displaced from one another about said circular track;

a first of said detectors disposed adjacent said suction head, a second of said detectors displaced angularly along said direction of rotation from said first detector by a first angle substantially equal to an angular rotation of said rotatable plate between samples, and a third of said detectors displaced angularly along said direction of rotation from said first detector at an angle greater than said first angle; and said timing means having means for moving said rotatable plate at a rate, from one sampling position to a next, of between about one day and two days, and for moving a sample from said one sampling position to a position adjacent said third of said detectors in substantially no less than five days.

19. The apparatus for collection of at least one filterable component and for determination of at least one parameter of said at least one filterable component according to claim 1 wherein said means for determining comprises at least one contamination detector, said at least one contamination detector being disposed above said suction head, such that said at least one contamination detector is aligned with said suction head.

20. The apparatus for collection of at least one filterable component and for determination of at least one parameter of said at least one filterable component according to claim 1 wherein said means for determining comprises at least one contamination detector, said at least one contamination detector being displaceable above said filtering means and adjustable as requested along said circular track of said rotatable plate.

21. The apparatus for collection of at least one filterable component and for determination of at least one parameter of said at least one filterable component according to claim 1 wherein said mat of filter material comprises a substantially circular filter mat.

22. An apparatus for collection of a specimen for measurement of at least one filterable component and for determination of at least one parameter of said at least one filterable component, said apparatus including two chambers, each chamber comprising:

a substantially rigid rotatable plate having formed thereon a circular track of throughgoing apertures;

a base for rotatably supporting said rotatable plate;

a suction head disposed on a first side of said rotatable plate to draw gas through a predetermined number of said apertures, the opposed contact surfaces of said suction head and said circular track being substantially flat and smooth to thereby minimize frictional forces between said contact surfaces;

a mat of filter material disposed in contact with said circular track of apertures on a second side of said rotatable plate opposite to said first side, said mat of filter material being supported by said rotatable plate and overlaying at least said circular track of apertures;

means for stepwisely rotating said rotatable plate with respect to said base, including a second rotatable plate having a toothed rim rigidly connected to said first rotatable plate and solenoid means for engagement with said toothed rim of said second rotatable plate for stepwisely rotating both of said rotatable plates;

means for determining said at least one parameter of said at least one filterable component, said determination means including at least one contamination detector disposed adjacent and aligned with said suction head;

means for biasing said suction head against said rotatable plate, said biasing means having spring means for continuously aligning said suction head against said rotatable plate, said plate defining a first substantially flat planar surface and said head defining a second substantially flat planar surface disposed against said first surface;

said suction head having a lip, said lip having a width for substantially preventing binding between said head and said rotatable plate, and also for providing sealing contact between said first surface on said plate and said second surface on said head, whereby leakage of gas between said suction head and said rotatable plate is minimized;

said head having a longitudinal axis being substantially aligned with an axis substantially perpendicular to said first surface;

said head being angularly displaceable with respect to said axis perpendicular to said first surface; and said spring means including alignment means for aligning said second surface with respect to said first surface and for providing substantially sealing contact therebetween;

said alignment means including an angularly and axially self-aligning spring structure;

timing means for energizing said rotating means along a direction of rotation at predetermined times; and means for operating said two chambers alternately.

23. The apparatus for collection of at least one filterable component and for determination of at least one parameter of said at least one filterable component according to claim 22 wherein said mat of filter material comprises a substantially circular sheet of filter mat.

* * * * *